US009308252B2

(12) United States Patent
Suckow et al.

(10) Patent No.: US 9,308,252 B2
(45) Date of Patent: Apr. 12, 2016

(54) EXTRACELLULAR MATRIX MATERIALS AS VACCINE ADJUVANTS FOR DISEASES ASSOCIATED WITH INFECTIOUS PATHOGENS OR TOXINS

(75) Inventors: Mark A. Suckow, Granger, IN (US); William R. Wolter, South Bend, IN (US); Paul Hall, Lafayette, IN (US)

(73) Assignees: COOK BIOTECH, INC., West Lafayette, IN (US); UNIVERSITY OF NOTRE DAME, Notre Dame, IN (US)

( * ) Notice: Subject to any disclaimer, the term of this patent is extended or adjusted under 35 U.S.C. 154(b) by 1040 days.

(21) Appl. No.: 11/699,448

(22) Filed: Jan. 30, 2007

(65) Prior Publication Data

US 2008/0107665 A1    May 8, 2008

Related U.S. Application Data

(63) Continuation-in-part of application No. 11/583,771, filed on Oct. 20, 2006, now Pat. No. 8,778,360.

(60) Provisional application No. 60/730,379, filed on Oct. 27, 2005.

(51) Int. Cl.
*A61K 39/39* (2006.01)
*A61K 39/08* (2006.01)
*A61K 39/00* (2006.01)

(52) U.S. Cl.
CPC .......... *A61K 39/39* (2013.01); *A61K 39/08* (2013.01); *A61K 2039/55511* (2013.01); *A61K 2039/55588* (2013.01)

(58) Field of Classification Search
None
See application file for complete search history.

(56) References Cited

U.S. PATENT DOCUMENTS

| | | | |
|---|---|---|---|
| 2,172,903 A | 9/1939 | Charping | |
| 3,346,401 A | 10/1967 | Barat et al. | |
| 3,562,820 A | 2/1971 | Braun | |
| 3,810,473 A | 5/1974 | Cruz, Jr. et al. | |
| 4,502,159 A | 3/1985 | Woodroof et al. | |
| 4,578,067 A | 3/1986 | Cruz, Jr. et al. | |
| 4,902,508 A | 2/1990 | Badylak et al. | |
| 4,956,178 A | 9/1990 | Badylak et al. | |
| 5,028,695 A | 7/1991 | Eckmayer et al. | |
| 5,275,826 A | 1/1994 | Badylak et al. | |
| 5,281,422 A | 1/1994 | Badylak et al. | |
| 5,336,616 A | 8/1994 | Livesey et al. | |
| 5,352,463 A | 10/1994 | Badylak et al. | |
| 5,372,821 A | 12/1994 | Badylak et al. | |
| 5,437,287 A | 8/1995 | Phillips et al. | |
| 5,460,962 A | 10/1995 | Kemp | |
| 5,480,424 A | 1/1996 | Cox | |
| 5,507,810 A | 4/1996 | Prewett et al. | |
| 5,554,389 A | 9/1996 | Badylak et al. | |
| 5,733,337 A | 3/1998 | Carr, Jr. et al. | |
| 5,782,914 A | 7/1998 | Schankereli | |
| 5,837,269 A | 11/1998 | Daynes et al. | |
| 6,120,991 A * | 9/2000 | Carter et al. | 435/6 |
| 6,156,305 A | 12/2000 | Brauker et al. | |
| 6,206,931 B1 | 3/2001 | Cook et al. | |
| 6,207,147 B1 | 3/2001 | Hiserodt et al. | |
| 6,218,166 B1 | 4/2001 | Ravindranath et al. | |
| 6,264,992 B1 | 7/2001 | Voytik-Harbin et al. | |
| 6,277,368 B1 | 8/2001 | Hiserodt et al. | |
| 6,403,104 B1 | 6/2002 | Berd et al. | |
| 6,406,689 B1 | 6/2002 | Falkenberg et al. | |
| 6,451,971 B1 | 9/2002 | Akiyama et al. | |
| 6,548,066 B1 | 4/2003 | Michaeli et al. | |
| 6,699,483 B1 | 3/2004 | Dalgleish et al. | |
| 7,015,205 B1 | 3/2006 | Wallack et al. | |
| 7,090,853 B2 | 8/2006 | Kapp et al. | |
| 7,175,652 B2 | 2/2007 | Cook et al. | |
| 7,550,004 B2 | 6/2009 | Bahler et al. | |
| 2001/0006631 A1 | 7/2001 | Hiserodt et al. | |
| 2002/0001595 A1* | 1/2002 | Sonntag et al. | 424/208.1 |
| 2004/0013712 A1 | 1/2004 | Parma | |
| 2006/0099675 A1 | 5/2006 | Benard | |
| 2006/0265053 A1 | 11/2006 | Hunt | |
| 2007/0128174 A1* | 6/2007 | Kleinsek et al. | 424/93.7 |
| 2008/0107665 A1 | 5/2008 | Suckow et al. | |

(Continued)

FOREIGN PATENT DOCUMENTS

| | | |
|---|---|---|
| AU | 2007309193 | 5/2008 |
| AU | 2007345673 | 8/2008 |

(Continued)

OTHER PUBLICATIONS

Abraham et al (2000). J Biomed Mater Res, 51: pp. 442-452.*
Higaki et al (2001) Vaccine, 19: pp. 3091-3096.*
Boring, CC et al., "Cancer Statistics," CA Cancer Journal for Clinicians, 1993, vol. 43, pp. 7-26.
Nomura, Abraham et al., "Serum Selenium and Subsequent Risk of Prostate Cancer," Cancer Epidemiology, Biomarkers & prevention, Sep. 2000, vol. 9, pp. 883-887.

(Continued)

*Primary Examiner* — Michelle S Horning
(74) *Attorney, Agent, or Firm* — Husch Blackwell LLP; Denise L. Mayfield

(57) ABSTRACT

Disclosed are vaccines and vaccine adjuvants useful in the treatment and/or prevention of infection and diseases associated with infectious pathogens, such as tetanus, as well as diseases associated with biological toxins. Also provided are methods of preparing an adjuvant and the vaccine containing the adjuvant. Methods are also provided for vaccinating/immunizing an animal against infection and diseases associated with infectious pathogens, such as tetanus, and other diseases associated with biological toxins. Adjuvant materials are presented that are prepared from an extracellular matrix material. The adjuvants are demonstrated to enhance the immunogenicity of an infectious pathogen antigen or biological toxin antigen of interest, as well as to enhance the survival of an immunized animal.

16 Claims, 3 Drawing Sheets

(56) References Cited

U.S. PATENT DOCUMENTS

Figure 1:
Figure 2:
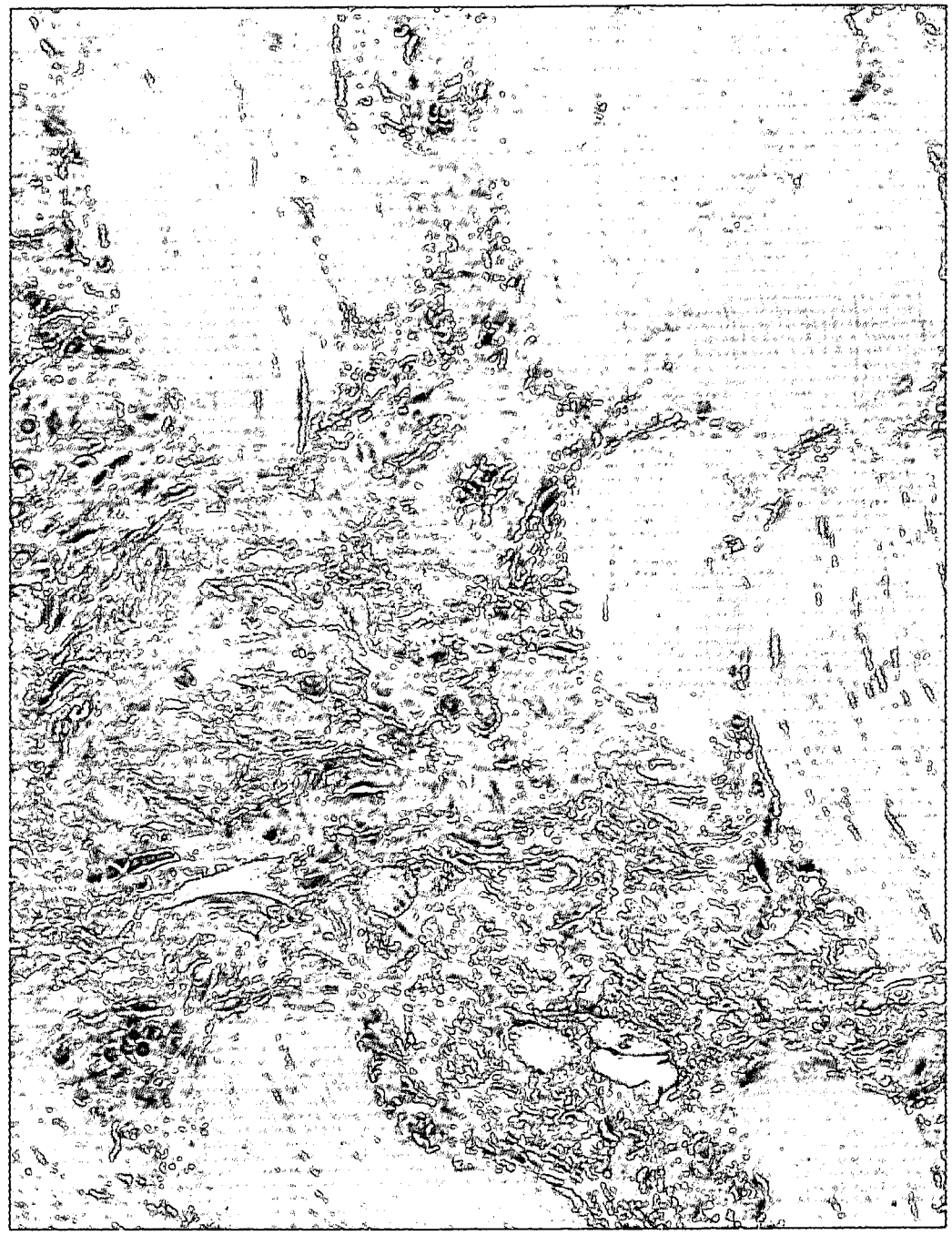
Figure 3:
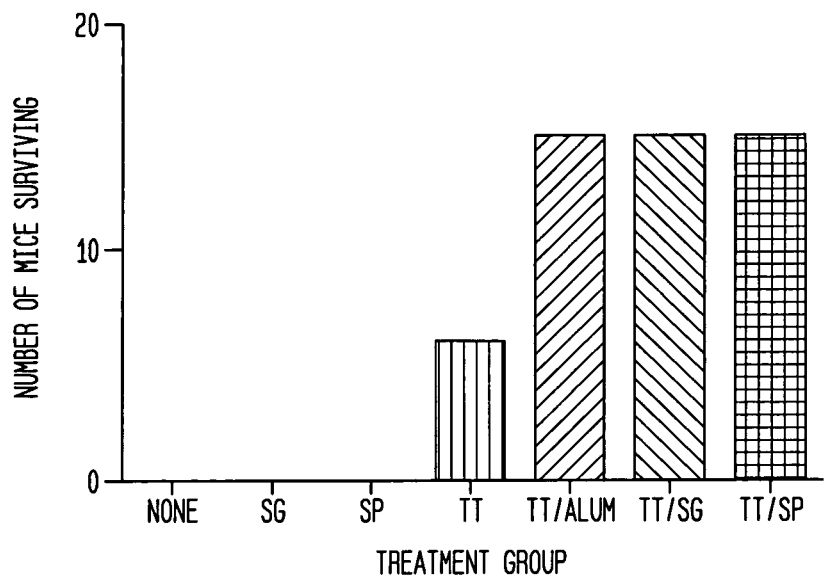

| | | | |
|---|---|---|---|
| 2008/0160049 | A1 | 7/2008 | Suckow et al. |
| 2008/0260800 | A1 | 10/2008 | Suckow et al. |
| 2009/0220461 | A1 | 9/2009 | Suckow et al. |
| 2009/0248144 | A1 | 10/2009 | Bahler et al. |
| 2010/0136050 | A1 | 6/2010 | Suckow et al. |
| 2010/0233214 | A1 | 9/2010 | Suckow et al. |
| 2011/0076305 | A1 | 3/2011 | Suckow et al. |
| 2011/0135690 | A1 | 6/2011 | Suckow |
| 2011/0150934 | A1 | 6/2011 | Suckow |

FOREIGN PATENT DOCUMENTS

| | | |
|---|---|---|
| CA | 2667075 | 5/2008 |
| CA | 2627364 | 7/2008 |
| CN | 101730541 | 6/2010 |
| EP | 2109667 | 10/2009 |
| EP | 21144444 | 11/2009 |
| JP | 2010507584 | 3/2010 |
| JP | 516763 | 5/2010 |
| WO | WO97/36495 | 10/1997 |
| WO | WO03/100034 | 12/2003 |
| WO | 2008051852 | 5/2008 |
| WO | 2008094276 | 8/2008 |
| WO | 2008112344 | 9/2008 |
| WO | 2009108656 | 9/2009 |

OTHER PUBLICATIONS

Brooks, James D., et al., "Plasma Selenium Level Before Diagnosis and the Risk of Prostate Cancer Development," Journal of Urology, Dec. 2001, vol. 166, pp. 2034-3038.
Hursting, Steven D., et al., "Types of Dietary Fat and the Incidence of Cancer at Five Sites," Preventive Medicine, (1990), vol. 19, pp. 242-253.
Gann, Peter H., et al., "Lower Prostate cancer Risk in Men with Elevated Plasma Lycopene levels: results of a Prospective Analysis," JAMA, May 12, 2999, vol. 281, No. 18, p. 1682.
Gann, Peter et al. "Lower Prostate Cancer Risk in men with Elevated Plasma Lycopene Levels: results of a Prospective Analysis," Cancer Research, Mar. 15, 1999, vol. 59, pp. 1225-1230.
Tjoe, B.A. et al., "Follow-Up Evaluation of a Phase II Prostate Cancer vaccine Trial," The Prostate, (1999), vol. 40, pp. 125-129.
Tjoe, Benjamin A. et al., "development of a Dendritic-Cell Based Prostate Cancer vaccine," Immunology Letters, (2000), vol. 74, pp. 873-93.
Gulley, James et al., "Phase I Study of a Vaccine Using recombinant Vaccinia Virus Expressing PSA (rV-PSA) in Patients with Metastatic Androgen-Independent Prostate Cancer," The Prostate, (2002), vol. 53, pp. 109-117.
Pollard, Morris & Luckert, Phyllis, "transplantable Metastasizing Prostate Adenocarcinomas in Rats," Journal of the National Cancer Institute, Mar. 1975, vol. 54, No. 3, pp. 643-649.
Suckow, Mark et al., "Heat-Labile Toxin-Producing Isolates of *Pasteurella multocida* From Rabbits," Laboratory Animal Science, Apr. 1991, vol. 41, No. 2, pp. 151-156.
Ringler, Daniel et al., "Protection of Rabbits against Experimental Pasteurellosis by Vaccination with a potassium Thiocyanate Extract of *Pasteurella multocida*," Infection and Immunity, Sep. 1985, vol. 49, No. 3, pp. 498-504.
Pollard, Morris & Luckert, Phyllis, "Production of Autochthonous Prostate Cancer in Lobund-Wistar rats by Treatments with N-Ntroso-N-methylurea and Testosterone," JNCI, Aug. 1986, vol. 77, No. 2, pp. 583-587.
Pollard, Morris & Luckert, Phyllis, "Autochthonous Prostate Adenocarcinomas in Lobund-Wistar Rats; A Model System," The Prostate, (1987), vol. 11, pp. 219-227.
Pollard, Morris, "Lobund-Wistar Rat Model of Prostate Cancer in Man," The Prostate, (1998), vol. 37, pp. 1-4.
Hrouda, D. et al., "*Mycobacterium vaccae* (SRL172): a Potential Immunological Adjuvant Elevated in Rat Prostate Cancer," British Journal of Urology, (1998), vol. 82, pp. 870-876.

Hrouda, D. et al., "Allogeneic Whole-Tumor Cell Vaccination in the Rat Model of Prostate Cancer," BJU International, (2000), vol. 86, pp. 742-748.
Griffith, Thomas S. et al., "Inhibition of Murine Prostate Tumor Growth and Activation of Immunoregulatory Cells with Recombinant Canarypox Viruses," Journal of the National Cancer Institute, Jul. 4, 2001, vol. 93, No. 13, pp. 998-1007.
Charles, Linda G. et al., "Antitumor Efficacy of Tumor-Antigen-Encoding Recombinant Poxvirus Immunization in Dunning Rat Prostate Cancer: Implications for Clinical Genetic Vaccine Development," World J. Urol., (2000), vol. 18, pp. 136-142.
Michael, Agniesla et al., "Delayed Disease Progression after Allogeneic Cell Vaccination in Hormone-Resistant Prostate Cancer and Correlation with Immunologic Variables," Clin. Cancer. Res., Jun. 15, 2005, vol. 11, No. 12, pp. 469-4478.
Wang, Z. et al., "Lack of HLA Class I Antigen Expression by Melanoma Cells SK-Mel-33 Caused by Reading a Frameshift in $\beta_2$-Microglobulin Messenger RNA," J. Clin. Invest., Feb. 1993, vol. 91, pp. 648-692.
Shekhar, Malathy et al., "Breast Stroma Plays a Dominant Regulatory Role in Breast Epithelial Growth and Differentiation: Implications for Tumor Development and Progression," Cancer Research, Feb. 15, 2001, vol. 61, pp. 1320-1326.
Cunha, Gerald R. et al., "Role of the Stromal Microenvironment in Carcinogenesis of the Prostate," Int. J. Cancer, (2003), vol. 107, pp. 1-10.
Wei, Yu-Quan, "Immunotherapy of Tumors with Vaccines based on Xenogeneic Homologous Molecules," Anti-cancer Drugs, (2002), vol. 13, pp. 119-235.
Fong, Lawrence et al., "Dendritic Cell-Based Xenoantigen Vaccination or Prostate Cancer Immunotherapy," The Journal of Immunology, (2001), vol. 167, pp. 7150-7156.
Srinivasan, Roopa et al., "Tumor Antigens for Cancer Immunotherapy: Therapeutic Potential of Xenogeneic DNA Vaccines," Journal of Translational Medicine, 2004, vol. 2, pp. 1-12.
Bergman, Phillip J. et al., "Long-Term Survival of Dogs with Advanced Malignant Melanoma After DNA Vaccination with Xenogeneic Human Tyrosinase: A Phase I Trial," Clinical Cancer Research, Apr. 2003, vol. 9, pp. 1284-1290.
He, Qiu-ming et al., "Inhibition of Tumor Growth with a Vaccine based on Xenogeneic Homologous Fibroblast Growth Factor Receptor-1 in Mice," Journal of Biological Chemistry, Jun. 13, 2003, vol. 24, pp. 21831-21836.
Fernandez-Acenero, M.J. et al., "Prognostic Influence of Tumor-Associated Eosinophilic Infiltrate in Colorectal Carcinoma," Cancer, (2002) vol. 88, pp. 1544-1548.
Ohashi, Yusuke et al., "Significance of Tumor Associated Tissue Eosinophilia and Other Inflammatory Cell Infiltrate in Early Esophageal Squamous Cell Carcinoma," Anticancer Research, (2002), vol. 20, pp. 3025-33030.
Furbert-Harris, Paulette et al., "Inhibition of Prostate Cancer Cell Growth by Activated Eosinophils," The Prostate, (2003), vol. 57, pp. 165-175.
Aguzzi, et al., "Pathogenesis of Prion Diseases: Current Status and Future Outlook", *Microbiology*, (2006), vol. 4, pp. 765-775.
Caughey, et al., "Prions and their Partners in Crime", *Nature*, (2006) vol. 44, pp. 803-810.
Edwards B.K., et al., *J Natl Cancer Inst* (2005); 97(19):1407-27.
Greenlee RT, Harmon M.B., Murray T, Thun M., "Cancer Statistics", (2001), *CA Cancer J Clin.*, (2001);51:15-36.
Simons J.W., Sacks N., *Urol. Oncol.*, (2006);24:419-424.
Fukino K, et al., *Cancer Res.*, (2004);64(20):7231-6.
Bissell MJ, et al., *J. Cell Sci. Suppl.*, (1987);8(3):327-43.
Matrisian LM, et al., *Cancer Res.*, (2001);61(9):3844-6.
Shekhar MP, et al., *Cancer Res.*, (2001);61(4):1320-6.
Tatenhorst L, et al. "Genes Associated with Fast Glioma Cell Migration in vitro and in vivo", *Brain Pathol.*, (2005);15(1):46-54.
Moschella F, et al., *Oncol Res.*, (2003);14(3):133-45.
Brewer J.M., "How do Aluminum Adjuvants Work?" *Immunol Lett.*, (2006); 102(1):10-5.
Lindblad, EB., *Immunol Cell Biol.*, (2004);82(5):497-505.
Barr, TA, et. al., Vaccine, (2006); 24(17):3399-407.
Hodge, J.W., *Front Biosci.*, (2006); 11:788-803.

(56) References Cited

OTHER PUBLICATIONS

Knoll L.D., *Urology*, (2001);57:753-757.
Knoll L.D., *Urology*, (2002);59:758-761.
Mantovani F, et al., *Eur. Urol.*, (2003);44:600-602.
O'Connor RC, Patel RV, Steinberg GD., *J Urology*, (2001);165:1995.
O'Connor RC, Hollowell CM, Steinberg GD., *Urology*, (2002);60:697x-697xii.
O'Connor RC, Harding JN, Steinberg GD., *Urology*. (2002);60:906-909.
Paradiso M, et. al., *Arch Ital Urol. Androl.*, (2003);75:116-118.
Weiser AC, et aL, *J. Urol*, (2003);170:1593-1595.
Oasis, Benbow M., "An Innovative Alternative Dressing for Chronic Wounds", *Br. J. Nurs.*, (2001);10:1489-1492.
Brown-Etris M, Cutshall WD, Hiles M.C., *Wounds*, (2002);14:150-166.
Schultz DJ, et al., *J. Am. Coll. Surg.*, (2002); 194:541-543.
Suckow M.A., of al., *Journal of Investigative Surgery*, (1999); 12:277-287.
Badylak, S.F., *Small Intestinal Submucosa (SIS): A Biomaterial Conducive to Smart Tissue Remodeling, Tissue Engineering: Current Perspectives*, Bell E (ed). Burkhauser Publishers, Cambridge, MA., (1993), pp. 179-189.
Badylak, S.F., "The Extracellular Matrix as a Scaffold for Tissue Reconstruction", *Seminars in Cellular and Developmental Biology*, (2002); 13:377-383.
Suckow MA, Hodde JP, Wolters WR, Hiles MC., *J.Wound Care*, (2005),14:137-140.
Suckow MA, Hodde JP, Wolter WR, Hiles MC., "Surgical Repair of Experimental Achilles Tenotomy with Porcine Renal Capsule Material in a Rat Model" *J.Mater Sci. Mater. Med.*
Lantz, G.C., et al., *J. Invest. Surg.*, (1993), 6:297.
Badylak, S.F., Lantz, G., Coffey, A., and Geddes, L.A., *J. Surg. Res.*, (1989), 47:74.
Lantz, G.C., Badylak, S.F., Coffey, A.C., Geddes, L.A., Blevins, W.E., *J. Invest. Surg.*, (1990), 3:217.
Hodde, J.P., and Hiles, M.C., *Biotechnol. Bioeng.*,(2002), 79:211.
Pollard M, Suckow M.A., "Hormone-Refractory Prostate Cancer in the Lobound-Wistar Rat", *Experimental Biology and Medicine*, (2005), 230:520-526.
Suckow MA, Wolter WR, Pollard M., *Cancer Immunology and Immunotherapy*, (2005); 54:571-576.
Pollard M, Lucked P.H., *J. Natl. Cancer Inst.*, (1975); 54:643-49.
Badylak SF, Record R, Lindberg K, Hodde J, Park K., *Journal of Biomaterials Sciences Polymer Edition*, (1998); 9:863-878.
Hodde, JP., et al., *J. Surg. Res.*, (2004); 120: 189-194.
Culora GA, Ramsay AD, Theaker JM., *J. Clin. Pathol.*, (1996); 49:844-845.
McDevitt CA, Wildey GM, Cutrone RM., *J. Biomed. Mater. Res.*, (2003);67A:637-646.
Bello-DeOcampo D, Tindall D.J., "TGF-beta/Smad signaling in Prostate Cancer", *Curr. Drug Targets*, (2003);41 97-210.
Voytik-Harbin S.L., et al., *Tissue Eng.*, (1998);4:157-174.
Michael A., et al., *Clin, Cancer Res.* (2005); 11:4469-4478.
Pilla L, et al., *Cancer Immunol Immunother.*, (2006);55:958-968.
Berd D, et al., *J. Clin Oncol.*, (1997);15:2359-2370.
Petrovsky N., *Vaccine*, (2006);24 Suppl. 2:S2-26-9.
Bendandi, M. et al., *Leuk. Lymphoma.*, (2006);47:29-37.
Redfern C.H., et al. *J Clin Oncol.*, (2006);24:3107-12.
Totterman TH, Loskog A, Essand M., *BJU Int.*, (2005);96:728-735.
Mosolits S, Nilsson B, Mellstedt H., "Towards Therapeutic Vaccines for Colorectal Carcinoma: A Review of Clinical Trials" *Expert Rev. Vaccines*, (2005);4:329-350.
He X, Tsang TC, Zhang T, Luo P, Harris DT., *Vaccine*, (2004);23:1966-1972.
Wei Y, Sticca R.P., et al., *Int. J. Oncol.*, (2006);28:585-593.
Rousseau RF, et al., *Blood*, (2006);107:1332-1341.
Akhurst, Rosemary, *J. Clin. Invest.* (2002); 1533-1536.
Kenney RT, et al., *J. Infect. Dis.*, (2004);190:774-782.
Skountzou I, et al., *Vaccine*, (2006);24:6110-6119.
Glenn GM, Kenney R.T., *Curr. Topics Microbiol. Immunol.*, (2006);304:247-268.
Rechsteiner G, et al., *J. Immunol.*, (2005);174:2476-2480.
Huang C.M, et al., *Proteomics*, (2005);5:1013-1023.
Michael, et al., *Clin. Cancer Res.*, (2005);11:4469-4478.
International Search Report/PCT/US2007/069727 Apr. 12, 2007, Dec. 4, 2007.
Written Opinion of the International Searching Authority, PCT/US07/69727, Dec. 4, 2007.
Ruozi, et al. Intact collagen and atelocollagen sponges: Characterization and ESEM observation, 2007, Materials Science and Engineering 27: 802-810.
Hodde, et al. Small Intestinal Submucosa Does Not Promote PAIII Tumor Growth in Lobund-Wistar Rats, 2004, vol. 120, pp. 189-194, especially p. 190, $2^{nd}$ column.
Higaki, et al. Collagen minipellet as a controlled release delivery system for tetanus and diphtheria toxoid, 2001, vol. 19, pp. 3091-3096.
Abraham, et al. Evaluation of the porcine intestinal collagen layer as a biomaterial, 1999, vol. 29, pp. 442-452.
International Search Report, PCT/US09/35062, dated Jul. 22, 2009.
International Search Report, mailed Jul. 22, 2009 in PCT/US 09/35062.
Aguzzi et al., (2003), "Immune system and peripheral nerves in propagation of prions to CNS," *Br Med Bull.*, 2003;66:141-59.
Allman et al., (2001), "Xenogeneic extracellular matrix grafts elicit a TH2-restricted immune response," *Transplantation*, 71:1631-1640.
Arbel et al., (2003), "Generation of antibodies against prion protein in wild-type mice via helix 1 peptide immunization," *J Neuroimmunol.*, 144(1-2):38-45.
Baars et al., (2000), "Skin tests predict survival after autologous tumor cell vaccination in metastatic melanoma: experience in 81 patients," *Ann. Oncol.* 11:965-970.
Banzhoff et al., (2003), "A new MF59-adjuvanted influenza vaccine enhances the immune response in the eldery with chronic diseases: results from an immunogenicity meta-analysis," *Gerontology*, 49(3):177-84.
Ben-Efraim et al., (2000), "Use of xenogenized (modified) tumor cells for treatment in experimental tumor and in human neoplasia," *Biomed & Pharmacotherapy*, 54:268-273.
Berd et al., (1990), "Treatment of metastatic melanoma with an autologous tumor-cell vaccine: clinical and immunologic results in 64 patients," *J. Clin. Oncol.*, 8:8158-1867.
Berraondo et al., (2007), "Eradication of large tumors in mice by a tritherapy targeting the innate, adaptive, and regulatory components of the immune system," *Cancer Res.*, 67:8847-8855.
Bodey et al., (2000), "Failure of cancer vaccines: the significant limitations of this approach to immunotherapy," *Anticancer Res.*, 20:2665-2676.
Brando et al., (2007), "Murine immune responses to liver-stage antigen 1 protein FMP011, a malaria vaccine candidate, delivered with adjuvant AS01B or AS02A," *Infect Immun.*, 75(2):838-45.
Burch et al., (2000), "Priming tissue-specific cellular immunity in a phase I trial of autologous dendritic cells for prostate cancer," *Clin. Cancer Res.*, 6:2175-2182.
Burch et al., (2004), "Immunotherapy (APC8015, Provenge) targeting prostatic acid phosphatase can induce durable remission of metastatic androgen-independent prostate cancer: a phase 2 trial," *Prostate* 60:197-204.
Caglar et al., (2005), "Effect of monophosphoryl lipid A on antibody response to diphtheria toxin and its subunits," *APMIS*. 113(4):256-63.
Chang et al., (2000), "Antigen-Specific Cancer Immunotherapy Using a GM-CSF secreting allogeneic tumor cell-based vaccine," *Int. J. Cancer*, 86:725-730.
Chatterjee et al., (1994), "Idiotypic antibody immunotherapy of cancer," *Cancer Immunol. Immunother.*, 38:75-82.
Corman et al., (1998), "Recognition of prostate-specific antigenic peptide determinants by human CD4 and CD8 T cells," *Clin. Exp. Immunol.*, 114:166-172.
Correale et al., (1997), "In vitro generation of human cytotoxic T lymphocytes specific for peptides derived from prostate-specific antigen," *J. Natl. Cancer Inst. USA*, 89:293-300.

(56) References Cited

OTHER PUBLICATIONS de Souza Matos et al., (2000), "Immunostimulatory effects of polar glycopeptidolipids of *Mycobacterium chelonae* for inactivated rabies vaccine," *Vaccine.* 18(20):2125-31.
Degruijl et al., (1999), "Cancer vaccine strategies get bigger and bigger," *Nature Medicine*, 5:1124-1125.
Denmeade et al., (2003), "Prostate specific antigen (PSA) does not affect growth of prostate cancer cells in vitro or prostate cancer xenografts in vivo," *Prostate.* 56:45-53.
Desai et al., (2000), "Immune response with biodegradable nanospheres and alum: studies in rabbits using staphylococcal enterotoxin B-toxoid," *J Microencapsul.*, 17(2):215-25.
Dillman et al., (1998), "Clinical experience with autologous tumor cell lines for patient-specific vaccine therapy in metastatic melanoma," *Cancer Biother. Radiopharm.*, 13:165-173.
Dillman et al., (2001), "Short-term cell lines from breast cancer for use as autologous tumor cell vaccines in the treatment of breast cancer," *Cancer Biotherapy & Radiopharmaceuticals*, 16:205-211.
Dols et al., (2003), "Vaccination of women with metastatic breast cancer using a costimulatory gene (CD80)-modified, HLA-A2 matched allogeneic, breast cancer cell line: clincal and immunological results," *Human Gene Therapy*, 14:1117-1123.
Donnelly, (2003), "Cancer vaccine targets leukemia," *Nature Medicine*, 9:1354-1356.
Eaton et al., (2002), "Allogeneic whole-cell vaccine: a phase I/II study in men with hormone-refractory prostate cancer," *British Journal of Urology*, 89:19-26.
Eldridge et al., (1991), "Biodegradable and biocompatible poly(DL-lactide-co-glycolide) microspheres as an adjuvant for staphylococcal enterotoxin B toxoid which enhances the level of toxin-neutralizing antibodies," *Infect Immun.*, 59(9):2978-86.
Enari et al., (2001), "Scrapie prion protein accumulation by scrapie-infected neuroblastoma cells abrogated by exposure to a prion protein antibody," *Proc Natl Acad Sci U S A*, 98(16):9295-9.
Evans et al., (1999), "Vaccine therapy for cancer—fact or fiction?" *Q. J. Med.*, 92:299-307.
Ezzell, (1995), "Cancer 'vaccines': an idea whose time has come?" *J NIH Res.*, 7:4-49.
Finn et al., (2002), "Prophylactic Cancer Vaccines," *Curr. Opin. Immunol.*, 14:172-177.
Flick-Smith et al., (2002), "Mucosal or parenteral administration of microsphere-associated Bacillus anthracis protective antigen protects against anthrax infection in mice," *Infect Immun.*, 70(4):2022-8.
Forni et al., (2000), "Immunoprevention of cancer," *Cancer Res.*, 60:2571-2575.
Frost et al., (1975), "Tumor immunoprophylaxis in mice using glutaraldehyde-treated syngenic tumor cells," *Cancer Res.*, 35:2646-2650.
Fuessel et al., (2006), "Vaccination with hormone-refractory prostate cancer patients with peptide cocktail-loaded dendritic cells: results of phase I clinical trial," *Prostate.* 66:811-821.
Gilch et al., (2003), "Polyclonal anti-PrP auto-antibodies induced with dimeric PrP interfere efficiently with PrPSc propagation in prion-infected cells," *J Biol Chem.*, 278(20):18524-31.
Granziero et al., (1999), "Adoptive immunotherapy prevents prostate cancer in a transgenic animal model," *Eur. J. Immunol.*, 29:1127-1138.
Griffiths et al., (1997), "Liposomally-encapsulated ricin toxoid vaccine delivered intratracheally elicits a good immune response and protects against a lethal pulmonary dose of ricin toxin," *Vaccine*, 15(17-18):1933-9.
Gu et al., (2002), "Substitution of porcine small intestinal submucosa for rabbit Achilles tendon, an experimental study," *Natl. Med. J. China*, 82:1279-1282 (Chinese language with English abstract).
Hahn et al., (2006), "Short-term dietary administration of celecoxib enhances the efficacy of tumor lysate-pulsed dendritic cell vaccines in treating murine breast cancer," *Int. J. Cancer*, 118:2220-2231.
Hanan et al., (2001), "Antiaggregating antibody raised against human PrP 106-126 recognizes pathological and normal isoforms of the whole prion protein," *Cell Mol Neurobiol.*, 21(6):693-703.
Hanan et al., (2001), "Immunomodulation of the human prion peptide 106-126 aggregation," *Biochem Biophys Res Commun.*, 280(1):115-20.
Harada et al., (2003), "Prostate-specific antigen-derived epitopes capable of inducing cellular humoral responses in HLa-A24+ prostate cancer patients," *Prostate*, 57:152-159.
Hedlund et al., (2001), "Negligible adjuvant effect for antibody responses and frequent adverse events associated with IL-12 treatment in humans vaccinated with pneumococcal polysaccharide," *Vaccine.* 20(1-2):164-9.
Higgins et al., (1996), "MF59 adjuvant enhances the immunogenicity of influenza vaccine in both young and old mice," *Vaccine*, 14(6):478-84.
Horiguchi et al., (2002), "Screening of HLA-A24-restricted epitope peptides from prostate-specific membrane antigen that induces specific antitumor cytotoxic T lymphocytes," *Clin. Cancer Res.*, 8:3885-3892.
Jaganathan et al., (2006), "Strong systemic and mucosal immune responses to surface-modified PLGA microspheres containing recombinant hepatitis B antigen administered intranasally," *Vaccine* 24(19):4201-11.
Jager et al., (2003), "Antigen-specific immunotherapy and cancer vaccines," *Intl. J. Cancer*, 106:817-820.
Jarvinen et al., (2000), "Intranasal vaccination of New Zealand white rabbits against pasteurellosis using alginate-encapsulated *Pasteurella multocida* toxin and potassium thiocyanate extract," *Comparative Medicine*, 50:263-269.
Jocham et al., (2004), "Adjuvant autologous renal tumour cell vaccine and risk of tumour progression in patients with renal-cell carcinoma after radical neprectomy: phase III, randomised controlled trial," *Lancet*, 363:594-599.
Kende et al., (2006), "Enhancement of intranasal vaccination in mice with deglycosylated chain A ricin by LTR72, a novel mucosal adjuvant," *Vaccine*, 15;24(12):2213-21.
Kenney et al., (1999), "Protective immunity using recombinant human IL-12 and alum as adjuvants in a primate model of cutaneous leishmaniasis," J Immunol., 163(8):4481-8.
Kobayashi et al., (2003), "Identification of naturally processed helper T-cell epitopes from prostate-specific membrane antigen using peptide-based in vitro stimulation," *Clin. Cancer Res.*, 9:5386-5393.
Kochenderfer et al., (2007), "Maximizing CD8+ T cell responses elicited by peptide vaccines containing CpG oligodeoxynucleotides," *Clin. Immunol.*, 124:119-130.
Koller et al., (2002), "Induction of antibodies against murine full-length prion protein in wild-type mice," *J Neuroimmunol.*, 132(1-2):113-6.
Komenaka et al., (2004), "Immunotherapy for melanoma," *Clinics in Dermatology*, 22:251-265.
Langermans et al., (2005), "Effect of adjuvant on reactogenicity and long-term immunogenicity of the malaria Vaccine ICC-1132 in macaques," *Vaccine*, 23(41):4935-43.
Lee et al., (1999), "Increased vaccine-specific T cell frequency after peptide-based vaccination correlates with increased susceptibility to in vitro stimulation but does not lead to tumor regression," *J. Immunol.*, 163:6292-6300.
Levesque et al., (2006), "Association between immunogenicity and adsorption of a recombinant Streptococcus pneumoniae vaccine antigen by an aluminum adjuvant," *Hum Vaccin.*, 2(2):74-7.
Lord et al., (2007), "Low dose metronomic oral cyclophosphamide for hormone resistant prostate cancer: a phase II study," *J. Urology*, 177:2136-2140.
Lu et al., (2002), "Rcognition of prostate tumor cells by cytotoxic T lymphocytes specific for prostate-specific membrane antigen," *Cancer Res.*, 62:5807-5812.
Lubaroff et al., (2006), "Decreased cytotoxic T cell activity generated by co-administration of PSA vaccine and CpG ODN is associated with increased tumor protection in a mouse model of prostate cancer," Vaccine, 24:6155-6162.
Martin, (1997), "Development of an adjuvant to enhance the immune response to influenza vaccine in the elderly," *Biologicals*, 25(2):209-131.

(56) References Cited

OTHER PUBLICATIONS

Matsueda et al., (2005), "Identification of peptide vaccine candidates for prostate cancer patients with HLS-A3 super-type alleles," *Clin. Cancer Res.*, 11:6933-6943.
McNeel et al., (2001), "Identification of T helper epitopes from prostatic acid phosphatae," *Cancer Res.*, 61:5161-5167.
Mendez et al., (2003), "Coinjection with CpG-containing immunostimulatory oligodeoxynucleotides reduces the pathogenicity of a live vaccine against cutaneous Leishmaniasis but maintains its potency and durability," *Infect Immun*, 71(9):5121-9.
Miller et al., (2006), "The role of melatonin in immuno-enhancement: potential application in cancer," *Int. J. Exp. Path.*, 87:81-87.
Moody et al., (1994), "Interleukin-2 transfected prostate cancer cells generate a local antitumor effect in vivo," *Prostate*. 24:244-251.
Mullen et al., (2006), "Enhancement of functional antibody responses to AMA1-C1/Alhydrogel, a Plasmodium falciparum malaria vaccine, with CpG oligodeoxynucleotide," *Vaccine*, 24(14):2497-505.
Ochsenbein et al., (1999), "Immune surveillance against a solid tumor fails because of immunological ignorance," *Proc. Natl. Acad. Sci. USA*, 96:2233-2238.
Okaji et al., (2004), "Vaccination with autologous endothelium inhibits angiogenesis and metastasis of colon cancer through autoimmunity," *Cancer Science*, 95:85-90.
Palese, (2006), "Making better influenza virus vaccines?" *Emerg Infect Dis.*, 12(1):61-5.
Peng et al., (2006), "Novel vaccines for the treatment of chronic HBV infection based on mycobacterial heat shock protein 70," Vaccin, 24(7):887-96.
Peretz et al., (2001), "Antibodies inhibit prion propagation and clear cell cultures of prion infectivity," *Nature* 412(6848):739-43.
Peters et al., (1979), "Preparation of immunotherapeutic autologous tumor cell vaccines from solid tumors," *Cancer Res.*, 39:1353-1360.
Petrik et al., (2007), "Aluminum adjuvant linked to Gulf War illness induces motor neuron death in mice," Neuromolecular Med., 9:83-100.
Pimenta et al., (2006), "Intranasal immunization with the cholera toxin B subunit-pneumococcal surface antigen A fusion protein induces protection against colonization with *Streptococcus pneumoniae* and has negligible impact on the nasopharyngeal and oral microbiota of mice," *Infect Immun.*, 74(8):4939-44.
Pollard et al., (2006), "Dietary prevention of hormone refractory prostate cancer in Lobund-Wistar rats: a review of studies in relevant animal model," *Comp. Med.*, 56:461-467.
Polymenidou et al., (2004), "Humoral immune response to native eukaryotic prion protein correlates with anti-prion protection," *Proc Natl Acad Sci U S A*,101 Suppl 2:14670-6.
Qin et al., (2004), "CpG ODN enhances immunization effects of hepatitis B vaccine in aged mice," Cell Mol Immunol., 1(2):148-52.
Rosado-Vallado et al., (2005), "Aluminium phosphate potentiates the efficacy of DNA vaccines against Leishmania mexicana," *Vaccine* 23(46-47):5372-9.
Rosset et al., (2004), "Breaking immune tolerance to the prion protein using prion protein peptides plus oligodeoxynucleotide-CpG in mice," *J Immunol.*, 172(9):5168-74.
Sabirov et al., (2006), "Intranasal vaccination of neonatal mice with polysaccharide conjugate vaccine for protection against pneumococcal otitis media," *Vaccine*, 24(27-28):5584-92.
Sanderson et al., (1974), "The induction of tumour immunity in mice using glutaraldehyde-treated tumor cells," *Nature*, 248:690-691.
Schwarz et al., (2004), "Immunisation with a synthetic prion protein-derived peptide prolongs survival times of mice orally exposed to the scrapie agent," *Neurosci Lett.*, 350(3):187-9.
Segura-Velázquez et al., (2006), "A novel synthetic adjuvant effectively enhances the immunogenicity of the influenza vaccine," *Vaccine*, 24(8):1073-80.
Sen et al., (2006), "Immunization of aged mice with a pneumococcal conjugate vaccine combined with an unmethylated CpG-containing oligodeoxynucleotide restores defective immunoglobulin G antipolysaccharide responses and specific CD4+-T-cell priming to young adult levels," *Infect Immun.*, 74(4):2177-86.
Sigurdsson et al., (2002), "Immunization delays the onset of prion disease in mice," *Am J Pathol.*, 161(1):13-7.
Simons et al., (1999), "Induction of immunity to prostate cancer antigens: results of a clnical trial of vaccination with irradiated autologous prostate tumor cells engineered to secrete granulocyte-macrophage colony-stimulating factor using ex vivo gene transfer," *Cancer Res.*, 59:5160-5168.
Simons et al., (2002), "Phase II trials of a GM-CSF genetransduced prostate cancer cell line vaccine (GVAX) in hormone refractory prostate cancer," *Proc. Am. Soc. Clin. Oncol.*, 21:183a (Abstract 729).
Singh et al., (1992), "Stroma is critical for preventing or permitting immunological destruction of antigenic cancer cells," *J. Exp. Med.*, 175:139-146.
Small et al., (2000), "Immunotherapy of hormone-refractory prostate cancer with antigen-loaded dendritic cells," *J. Clin. Oncol.*, 18:3894-3903.
Small et al., (2005), "Results of a placebo-controlled phase III trial of immunotherapy with APC8015 for patients with homrone refractory prostate cancer (HRPC)," *Proc. Am. Soc. Clin. Oncol.*, 23(16S):378S (Abstract 4500).
Souan et al., (2001), "Modulation of proteinase-K resistant prion protein by prion peptide immunization," *Eur. J. Immunol.*, 31(8):2338-46.
Stack et al., (1982), "Autologous X-irradiated tumor cells and percutaneous BCG in operable lung cancer," *Thorax*. 37:599-593.
Stewart et al., (2006), "Pre-clinical evaluation of new adjuvant formulations to improve the immunogenicity of the malaria vaccine RTS,S/AS02A," *Vaccine*, 24(42-43):6483-92.
Suckow et al., (2007), "Prevention of human PC-346C prostate cancer growth in mice by xenogeneic tissue vaccine," *Cancer Immunol. Immunother.*, 56:1275-1283.
Suckow et al., (2007), "Surgical Repair of Experimental Achilles Tenotomy with Porcine renal capsule material in a rat model," *J. Mater. Sci. Mater. Med.*, 18:1105-1110.
Suckow et al., (2007), "Tissue vaccines for cancer," *Expert. Rev. Vacc.*, 6:925-937.
Sugai et al., (2005), "A CpG-containing oligodeoxynucleotide as an efficient adjuvant counterbalancing the Th1/Th2 immune response in diphtheria-tetanus-pertussis vaccine," *Vaccine*, 23(46-47):5450-6.
Süli et al., (2004), "Experimental squalene adjuvant. I. Preparation and testing of its effectiveness," Vaccine, 22(25-26):3464-9.
Sung et al., (2006), "HBV-ISS (Dynavax)," *Curr Opin Mol Ther.*, 8(2):150-5.
Teir et al., (1957), "Effects of intraperitoneally injected suspension of roetgen irradiated and non-irradiated tumor tissue on the growth of homologous tissue," *Acta Pathol. Microbiol. Scand.*, 40:273-282.
Theeten et al., (2005), "Effects of lowering the aluminium content of a dTpa vaccine on its immunogenicity and reactogenicity when given as a booster to adolescents," *Vaccine*. 10;23(12):1515-21.
Vermorken et al., (1999), "Active specific immunotherapy for stage II and stage III human colon cancer: a randomized trial," *Lancet*, 353:345-350.
Vieweg et al., (1994), "Immunotherapy of prostate cancer in the Dunning rate model: use of cytokine gene modified tumor vaccines," *Cancer Res.*, 54:1760-1765.
Vitetta et al., (2006), "A pilot clinical trial of a recombinant ricin vaccine in normal humans," *Proc Natl Aead Sci U S A*, 103(7):2268-73.
Wilson et al., (1997), "Human prostate tumor angiogenesis in nude mice: metalloprotease and plasminogen activator activities during tumor growth and neovascularization of subcutaneously injected matrigel impregnated with human prostate tumor cells," *Anatomical Record*, 249:63-73.
Xue et al., (1997), "Induction of human cytotoxic T lymphocytes specific for prostate-specific antigen," *Prostate* 30:73-78.
Zhang et al., (2003), "Dendritic cells transfected with interleukin-12 and pulsed with tumor extract inhibit growth of murine prostatic carcinoma in vivo," *Prostate*, 55:292-298.
Written Opinion for International Application No. PCT/US2007/081962.

(56) References Cited

OTHER PUBLICATIONS

International Search Report for International Application No. PCT/US2007/081962.

Zhang, et al., "Physicochemical Properties of Collagen, Gelatin and Collagen Hydrolysate Derived from Bovine Limed Split Wastes," Journal of the Society of Leather Technologists and Chemists, received Sep. 2005, p. 23, vol. 90.

Davis, et al., "Regulation of Tissue Injury Responses by the Exposure of Matricryptic Sites within Extracellular Matrix Molecules," American Journal of Pathology, May 2000, pp. 1489-1498, vol. 156, No. 5.

Leikina, et al., "Type I Collagen in Thermally Unstable at Body Temperature," PNAS, Feb. 5, 2002, pp. 1314-1318; vol. 99, No. 3.

Hirota, et al., "Collagen of Chronically Inflamed Skin is Over-Modified and Upregulates Secretion of Matrix Metalloproteinase 2 and Matrix-Degrading Enzymes by Endothelial Cells and Fibroblasts," The Journal of Investigative Dermatology, Dec. 2003, pp. 1317-1325, vol. 121, No. 6.

German Office Action dated Jun. 28, 2011.

Folch, et al., "Microengineering of Cellular Interactions", Annu. Rev. Biomed. Eng. 02:227-256. 2000.

Zhang, et al., "Physicochemical Properties of Collagen, Gelatin and Collagen Hydrolysate Derived from Bovine Limed Split Wastes", Journal of the Society of Leather Technologists and Chemists., vol. 90, p. 23-28, 2006.

Telis, et al., "Characterizations of Collagen Fibers for Biodegradable Films Production", IUFoST World Congress, 13th World Congress of Food Science & Technology, iufost (2006). DOI:10.1051/IUFoST:20060929.

\* cited by examiner

EXTRACELLULAR MATRIX MATERIALS AS VACCINE ADJUVANTS FOR DISEASES ASSOCIATED WITH INFECTIOUS PATHOGENS OR TOXINS

CROSS-REFERENCE TO RELATED APPLICATIONS

This application is a continuation-in-part of U.S. patent application Ser. No. 11/583,771 entitled "Extracellular Matrix Cancer Vaccine Adjuvant", filed Oct. 20, 2006, which claims priority from U.S. Provisional Patent Application No. 60/730,379 entitled "Use of Extracellular Matrix Materials as a Vaccine Carrier and Adjuvant", filed Oct. 27, 2005. The entire disclosure and contents of the above applications are hereby incorporated by reference.

STATEMENT OF JOINT RESEARCH AGREEMENT

In compliance with 37 C.F.R. §1.71(g) (1), disclosure is herein made that the claimed invention was made pursuant to a Joint Research Agreement as defined in 35 U.S.C. 103 (c) (3), that was in effect on or before the date the claimed invention was made, and as a result of activities undertaken within the scope of the Joint Research Agreement, by or on the behalf of the University of Notre Dame and Cook Biotech, Inc. (West Lafayette, Ind.).

BACKGROUND

1. Field of the Invention

The present invention relates generally to vaccines that include an adjuvant, and to adjuvants alone. In particular, the invention relates to adjuvants derived or obtained at least in part from biological tissues, such as extracellular matrices, particularly small intestinal submucosa (SIS). The invention also relates to the field of methods for immunizing an animal against diseases associated with infectious pathogens, and infections by said pathogens, or toxins using a vaccine preparation that includes a tissue-derived adjuvant. The invention also relates to the field of methods for preparing adjuvants, as a method for preparing an adjuvant from small intestinal tissue for use as a part of a vaccine to immunize an animal against disease associated with an infectious agent, and in particular, against tetanus, as a vaccine for the treatment and/or prevention of tetanus, is provided.

2. Related Art

Aluminum hydroxide and aluminum phosphate (collectively referred to as alum) are routinely used as adjuvants in human and veterinary vaccines (1). The efficacy of alum in increasing antibody responses to diphtheria and tetanus toxins is well established (2) and Hepatitis B virus antigen vaccine has been adjuvinated with alum (3). While the usefulness of alum is well established for some applications, it has limitations. For example, alum is a poor inducer of Th1 cellular immune responses and stimulates the production of antibodies, which is consistent with Th2 cellular immune response (4-6). Unfortunately, a Th2 based immune response is not likely to offer optimal protection against several important infectious diseases, including tuberculosis (TB), human immunodeficiency virus (HIV) and hepatitis C virus (HCV). Alum is poorly effective for influenza vaccination and inconsistently elicits a cell mediated immune response. The antibodies elicited by alum-adjuvinated antigens are mainly of the IgG1 isotype in the mouse, which may be optimal for protection by some vaccinal agents.

Tetanus is an important human and animal disease characterized by painful, uncontrolled muscle spasms, and death due to paralysis of the respiratory muscles. This disease is associated with infection by *Clostridium tetani* and prophylactic vaccination is common. Tetanus vaccines typically use alum as an adjuvant.

A need continues to exist in the medical arts for materials that may be used to enhance and/or improve existing clinical alternatives to the treatment and prophylaxis of disease associated with infectious agents and toxins, for example, to improve existing forms of tetanus treatment vaccines and tetanus vaccine adjuvants with improved immunogenicity.

SUMMARY OF THE INVENTION

The present invention was developed in part by the inventors' recognition of the robust inflammatory response invoked by an extracellular matrix material (ECM) preparation, such as matrix isolated from the small intestinal submucosa (SIS). While not intending to be limited to any particular mechanism of action, the extracellular matrix material appears to provide the robust inflammatory response through, among other things, it's contribution of pro-inflammatory species that drive the immune response to the antigenic species that it is co-administered with. The present invention harnesses the inflammatory-provoking activity of ECM, such as SIS, and preparations from other forms of ECM, in the design of an immunopotent infectious agent vaccine preparation and infectious agent adjuvant.

The crafting of infectious agent vaccine preparations using ECM, and materials like it, may be used in combination with many different infectious pathogens or biological toxins. By way of example, and in some embodiments, the biological toxin is tetanus toxin. By further way of example, and in some embodiments, the biological toxin is ricin.

The present invention is unique in that, among other things, it involves the modification and use of a three-dimensional extracellular matrix material, and modified preparations thereof, to provide a vaccine. By way of example, and in some embodiments, the vaccine is a tetanus vaccine. The invention thus provides in some embodiments highly improved infectious agent preparations with an adjuvant material having an acceptable biocompatibility.

The adjuvant effect of the ECM, such as the SIS adjuvant preparation, extends to a vaccine administered to protect against diseases associated with an infectious pathogen or biological toxin. In some embodiments, the present invention provides an adjuvant comprising an SIS gel or particulate SIS. Administered together with tetanus toxoid, these preparations confer protective immunity in vivo to animals challenged with tetanus toxin.

Infectious Agent Adjuvant

In one aspect, the present invention provides an extracellular matrix (ECM) material, such as a modified preparation of SIS, as an infectious agent vaccine adjuvant. In some embodiments, these preparations may be described as essentially free of alum. In some embodiments, the ECM materials may be described as a modified preparation of SIS (diluted) about 2-fold to about 20-fold.

Infectious Agent Vaccine

In another aspect, the present invention provides an infectious agent vaccine comprising a preparation of an extracellular matrix material together with a preparation of an antigen of an infectious pathogen.

In one aspect of the invention, there is provided an adjuvant composition comprising an immunogenically enhancing preparation characteristic of an extracellular matrix material (ECM), particularly a preparation comprising an extracellular matrix derived from small intestinal submucosa (SIS) or renal capsule material (RCM). In particular embodiments, the adjuvant composition comprises an extracellular matrix material comprising a small intestinal submucosa tissue preparation. In some embodiments, the adjuvant composition comprises 1 part of an extracellular matrix material (ECM) and 9 parts of a pharmaceutically acceptable carrier solution. By way of example, such a carrier is sterile saline.

According to another aspect, there is provided a composition comprising an adjuvant and a antigen of interest. In some embodiments, the antigen is a toxoid antigen. In some embodiments, the vaccine may be described as a vaccine to protect against infectious pathogens, such as a tetanus vaccine, an influenza vaccine, a rabies vaccine, a viral hepatitis vaccine, a diphtheria vaccine, an anthrax vaccine, a *Streptococcus* pneumonia infection vaccine, a malaria vaccine, a leishmaniasis vaccine, or a Staphylococcal enterotoxin B toxicosis vaccine.

Biological Toxins

Examples of the biological toxins that may be used in the preparation of the vaccines of the present invention are provided below:

Abrin
Aflatoxins
Botulinum toxins
*Clostridium perfringens* episilon toxin
Conotoxins
Diacetoxyscirpenol
Ricin
Saxitoxin
Shigatoxin
Staphylococcal enterotoxins
Tetrodotoxin
T-2 Toxin
Diptheria toxin
Streptococcal toxins
Cholera toxin
Pertussis toxin
Pneumolysin In particular embodiments, the vaccine may be described as a vaccine to protect against diseases associated with biological toxins, such as ricin.

Prion-Associated Diseases:

In some embodiments, the invention provides an adjuvant preparation that is suitable for use in combination with a prion-associated disease. By way of example, such prion associated diseases include, all of which are classified as transmissible spongiform encephalopathies, bovine spongiform encephalopathy, scrapie, cervid chronic wasting disease and Creutzfeld-Jakob disease.

In other embodiments, the invention may be described as providing a vaccine to protect against disease associated with a viral infection. By way of example, the vaccines of the present invention may be formulated to provide a composition useful in the treatment and/or prevention of viral infections associated with influenza, rabies and viral hepatitis.

In other embodiments, the invention may be described as providing a vaccine to protect against diseases associated with a bacterial infection. By way of example, the vaccines of the present invention may be formulated to provide a composition useful in the treatment and/or prevention of bacterial infections associated with diseases such as diphtheria, anthrax, sepsis, pneumonia, otitis media and meningitis.

In other embodiments, the invention may be described as providing a vaccine to protect against diseases associated with a parasitic infection. By way of example, the vaccines of the present invention may be formulated to provide a composition useful in the treatment and/or prevention of a parasitic infection associated with the diseases of malaria and leishmaniasis.

In other embodiments, the invention may be described as providing a vaccine to protect against illnesses and/or diseases associated with exposure to a biological toxin. By way of example, the vaccines of the present invention may be formulated to provide a composition useful in the treatment and/or prevention of illness associated with exposure to biological toxins such as ricin (that causes respiratory distress) or exposure to Staphylococcal enterotoxin B (SEB) (that results in food poisoning).

Method of Preparing a Adjuvant and a Vaccine

In another aspect, the invention provides a method for preparing an infectious agent vaccine. In some embodiments, the method comprises preparing an adjuvant for vaccination against infectious agents and biological toxins as described herein, and combining the adjuvant with an immunizing antigen of interest. In some embodiments, the antigen of interest is a tetanus toxoid preparation.

Methods of Preventing, Treating, Inhibiting, and/or Immunizing an Animal against an Infectious Pathogen According to yet another broad aspect of the invention, a method for treating an animal having an infectious disease or at risk of contracting a disease or illness associated with exposure to an infectious pathogen. By way of example, diseases associated with exposure to an infection pathogen include tetanus, malaria, diphtheria, anthrax, sepsis, pneumonia, otitis media and meningitis. In some embodiments, the invention provides a method for immunizing an animal against tetanus. In yet another embodiment, the invention provides a method for inhibiting the severity of tetanus and/or preventing the onset of tetanus altogether.

Clinical Infectious Pathogen Treatment Preparations

In yet another aspect, the invention provides a variety of unique infectious pathogen treatment preparations. These infectious agent treatment preparations may take the form of a gel, a sheet, or an injectable preparation suitable for parenteral administration, combined with an appropriate antigen of interest.

The following abbreviations are used throughout the description of the present invention:

ECM—Extracellular Matrix;
HCV—Hepatitis C Virus;
HV—Human Immunodeficiency Virus
RCM—Renal Capsule Material
SIS—Small Intestinal Submucosa;
TB—Tuberculosis

BRIEF DESCRIPTION OF THE DRAWINGS

FIG. 1, according to some embodiments of the invention, presents a remnant of SIS extracellular matrix material in a rat 28 days after surgical implantation. The remaining biomaterial is surrounded by macrophages with occasional lymphocytes. Stained with H & E, 400×.

FIG. 2, according to some embodiments of the invention, presents the focus of mononuclear inflammation at the interface of an implant/tendon surface in a rat which underwent repair of Achilles tendon defect with RCM 7 days earlier. Stained with H & E, 200×.

FIG. 3, according to some embodiments of the invention, presents the survival data of mice, vaccinated with 0.03 micrograms of tetanus toxoid, following challenge with 1 ng/mouse of tetanus toxin intraperitoneally. Treatment groups are untreated (None); SIS gel (SG); SIS particulate (SP); tetanus toxoid (TT); TT with alum (TT/Alum); TT with SIS gel (TT/SG); and TT with SIS particulate (TT/SP). Each group consisted of 15 mice. All mice which were untreated or vaccinated with only SIS gel or SIS particulate died; six mice vaccinated with unadjuvanted tetanus toxoid survived, and all mice vaccinated with tetanus toxoid in alum, SIS gel, or SIS particulate survived. This represents a significant (P≤0.001) increase in number of mice surviving for the latter three groups compared to all other groups.

Figure 4:
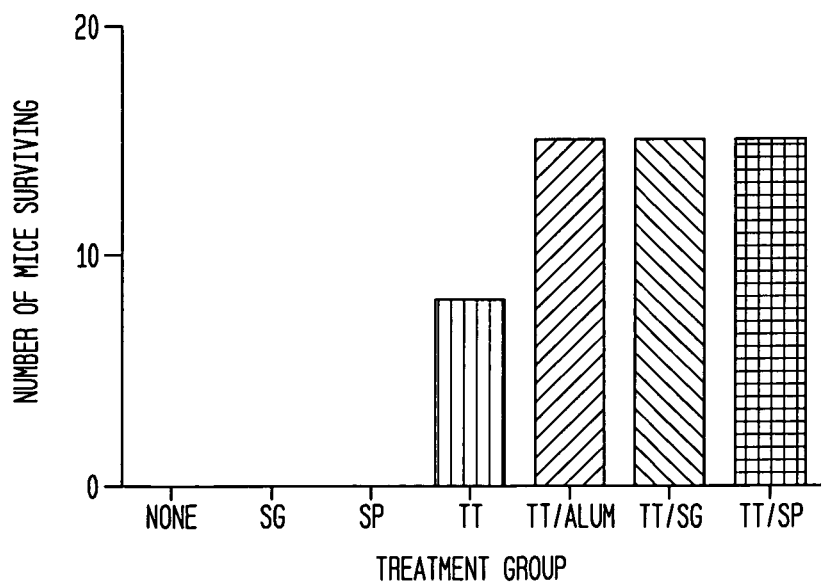

FIG. 4, according to some embodiments of the invention, presents survival data of mice, vaccinated with 0.05 micrograms of tetanus toxoid, following challenge with 1 ng/mouse of tetanus toxin intraperitoneally. Treatment groups are untreated (None); SIS gel (SG); SIS particulate (SP); tetanus toxoid (TT); TT with alum (TT/Alum); TT with SIS gel (TT/SG); and TT with SIS particulate (TT/SP). Each group consisted of 15 mice. All mice which were untreated or vaccinated with only SIS gel or SIS particulate died; eight mice vaccinated with unadjuvanted tetanus toxoid survived; and all mice vaccinated with tetanus toxoid in alum, SIS gel, or SIS particulate survived. This represents a significant (P≤0.001) increase in number of mice surviving for the latter three groups compared to all other groups.

DETAILED DESCRIPTION

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For the purposes of the present invention, the term "adjuvant" is defined as a substance which enhances the immune response to an antigen.

For purposes of the present invention, the term, "adjuvancy" is defined as the ability of an agent to enhance and/or promote the immune response of animal to a particular antigen.

For the purposes of the present invention, the term "biosynthetic material" is defined as a material that is in part or whole made up from or derived from a biological tissue.

For purposes of the present invention, the term "biological tissue" is defined as an animal tissue, including human, or plant tissue that is or that once was (cadaver tissue, for example) part of a living tissue or organism.

For the purposes of the present invention, the term "extracellular matrix" is defined as a tissue derived or bio-synthetic material that is capable of supporting the growth of a cell or culture of cells.

For the purposes of the present invention, the term "infectious agent" is defined as any bacterial, viral, prion or parasitic agent capable of causing disease in humans or animals subsequent to infection or secretion of a substance, such as the production of a toxin or toxins. This term also includes the toxic products of such agents. By way of example, such an infectious agent includes *clostridium botulinum*, the causative agent of tetanus.

For the purposes of the present invention, the term "biological toxin" is a poisonous substance, especially a protein that is produced by living cells or organisms and is capable of causing disease when introduced into the body tissues, such as ricin or Staphylococcal enterotoxin B and tetanus toxin.

For the purposes of the present invention, the term, "immunogenic amount" is an amount of an infectious pathogen antigen preparation of interest or amount of a biological toxin that elicits a clinically detectable protective response in an animal. By way of example, a clinically detectable protective response in an animal may be the production of an elevated titer of antibodies in the animal specific for the infectious pathogen antigen or biological toxin.

Description

A method for providing a preparation having an enhanced activity for inhibiting and protecting against an infectious pathogen provided. In particular embodiments, the infectious pathogen is tetanus.

A method for the treatment and/or inhibition of an infection caused by an infectious pathogen is also provided. In some embodiments, the method employs a composition comprising a vaccine, the vaccine comprising an adjuvant having a menu of pro-inflammatory species characteristic of an extracellular matrix (ECM) material together with an antigen associated with an infectious pathogen or a biological toxin. These preparations are found to be more immunogenic than use of the infectious pathogen antigen or biological toxin antigen vaccine alone in the treatment and/or prophylaxis against an infectious pathogen or biological toxin, such as tetanus.

The immune response to the described tetanus vaccine is enhanced by use of SIS as an adjuvant.

The description of the present invention is enhanced by the various examples that follow.

EXAMPLE 1

Materials and Methods for ECM as an Adjuvant for a Vaccine against Diseases Associated with an Infectious Pathogen The present example provides some examples of materials and methods that may be used in the practice of the present invention.

Small Intestinal Submucosa (SIS)

Small Intestinal Submucosa (SIS) was obtained from Cook Biotech, Inc. (West Lafayette, Ind.). Experimental grade material was provided for use in the present studies of an SIS preparation that was described as having been prepared by harvesting porcine jejunum and placing 10- to 20-cm lengths into saline solution (31-33). Following removal of all mesenteric tissues, the jejunal segment was everted and the tunica mucosa abraded using a longitudinal wiping motion with a scalpel handle and moistened gauze. The serosa and tunica muscularis were then gently removed using the same procedure. The remaining tissue was disinfected with peracetic acid, rinsed extensively in high purity water, and sterilized using ethylene oxide. SIS Particulate is supplied by Cook Biotech, Inc. (West Lafayette, Ind.) and is SIS material ground and sieved. The size particles are in the range from 45 micron to 335 micron. SIS gel is supplied by Cook Biotech, Inc. (West Lafayette, Ind.) and is produced from SIS material via an acid digestion and purification process.

Tetanus Toxin and Tetanus Toxoid

Tetanus toxin and tetanus toxoid were purchased from List Biological Laboratories (Campbell, Calif.).

Alum

Alum was purchased as Alhydrogel®, an aluminum hydroxide gel adjuvant (Brenntak Biosector, Frederikssund, Denmark).

Animals (Mice)—Statistical Analysis

Results of survival versus non-survival following challenge with tetanus toxin were compared between groups using the Chi-square test with two degrees of freedom. Differences were considered significant when p≤0.001.

EXAMPLE 2

Use of Adjuvant in the Inhibition of Tetanus

To determine if SIS can act as an adjuvant for vaccines against diseases associated with infectious pathogens or biological toxins, preparations were made with tetanus toxoid, an inactivated form of tetanus toxin. Both gel SIS and SIS particles produced from a sheet of single layer SIS were evaluated as adjuvants. Briefly, groups of 15 Balb/C female mice (Harlan, Inc., Indianapolis, Ind.) were vaccinated initially (0.1 ml volume/dose) and again, five weeks later with one of the following:
  Particulate SIS
  Gel SIS
  Tetanus toxoid (TT; 0.03 ug/dose)
  TT (0.05 ug/dose)
  TT (0.03 ug/dose)+alum (alhydrogel)
  TT (0.05 ug/dose)+alum (alhydrogel)
  TT (0.03 ug/dose)+particulate SIS
  TT (0.05 ug/dose)+particulate SIS
  TT (0.03 ug/dose)+gel SIS
  TT (0.05 ug/dose)+gel SIS
  Untreated control group Five weeks after the second vaccination, mice were challenged with a lethal dose of tetanus toxin (1 ng/mouse) given intraperitoneally in 0.2 ml of sterile saline. Mice were then observed over the next 96 hours and the number of surviving mice recorded for each group.

The results of this study are as follows:

| Treatment Group | Number Surviving/Total at 96 h |
|---|---|
| Untreated | 0/15 |
| Gel SIS | 0/15 |
| Particulate SIS | 0/15 |
| Tetanus toxoid (TT; 0.03 ug/dose) | 6/15 |
| TT (0.05 ug/dose) | 8/15 |
| TT (0.03 ug/dose) + alum (alhydrogel) | 15/15 |
| TT (0.05 ug/dose) + alum (alhydrogel) | 15/15 |
| TT (0.03 ug/dose) + particulate SIS | 15/15 |
| TT (0.05 ug/dose) + particulate SIS | 15/15 |
| TT (0.03 ug/dose) + gel SIS | 15/15 |
| TT (0.05 ug/dose) + gel SIS | 15/15 |

A significantly greater number of mice survived challenge with tetanus toxin in groups vaccinated with either 0.03 or 0.05 μg/dose of tetanus toxoid administered in alhydrogel, SIS gel, or particulate SIS compared to all other vaccination groups.

These results demonstrate the ability of both particulate and gel SIS to act as an adjuvant for a vaccine against disease associated with an infectious pathogen, such as tetanus.

EXAMPLE 3

Exemplary Infectious Pathogens

The present example demonstrates the utility of the present invention with disease associated with a wide variety of infectious pathogens and biological toxins, including by way of example and not exclusion, tetanus, influenza, rabies, viral hepatitis, diphtheria, anthrax, *Streptococcus pneumoniae* infection, malaria, leishmaniasis, ricin toxicosis, and Staphylococcal enterotoxin B toxicosis.

TABLE 2

Classification of Common Vaccines for Humans

| Disease or Pathogen | Type of Vaccine |
|---|---|
| Whole Organisms: | |
| Bacterial cells: | |
| Cholera | Inactivated |
| Plague | Inactivated |
| Tuberculosis | Attenuated BCG+ |
| *Salmonella typhi* | Attenuated |
| Viral Particles: | |
| Influenza | Inactivated |
| Measles | Attenuated |
| Mumps | Attenuated |
| Rubella | Attenuated |
| Polio (Sabin/OPV) | Attenuated |
| Polio (Salk/IPV) | Inactivated |
| *V. zoster* | Attenuated |
| Yellow fever | Attenuated |
| Type of Vaccine | |
| (Purified) Macromolecules | |
| Toxoids: | |
| Diphtheria | Inactivated exotoxin |
| Tetanus | Inactivated exotoxin |
| acellular Pertussis | Inactivated exotoxins |
| Capsular polysaccharide: | |
| Haemophilus influenzae b | polysaccharide + protein carrier |
| *Neisseria meningidis* | Polysaccaride |
| *Streptococcus pneumoniae* | 23 distinct capsular polysaccharides |
| Surface antigen: | |
| Hepatitis B | Recombinant surface antigen (HbsAg) |

+*Bacillus* Calmette-Guerin (BCG) is an antiviral strain of *Mycobacterium bovis*.

Vaccines for Disease Associated with Viral Infections

1. Influenza—Influenza is an acute febrile respiratory disease resulting from infection with the influenza virus. Current influenza vaccines use aluminum adjuvants. To enhance the efficacy of vaccines, several adjuvants have been examined. For example, the oil-in-water emulsion MF59 has been reported to improve vaccine immunity (Higgins (1996)[1]; Martin (1997)[2]), though it does not completely solve the low efficiency of the influenza vaccine in the elderly (Banzhoff (2003)[3]). A synthetic peptide, GK1, derived from *Taenia crassiceps cysticerci* was reported to enhance the immune response accompanying influenza vaccination in both young and aged mice (Segura-Velásquez (2006)[4]), but trials in humans have not been published.

As part of the present invention, an influenza vaccine may be provided that comprises the extracellular matrix material described herein as the vaccine adjuvant combined with an immunologically effective amount of an influenza antigen. By way of example, such an influenza antigen may comprise a current influenza virus combination of antigens of an H5N1 (hemagglutinin [HA] subtype 1; neuraminidase [NA] subtype 1), and H3N2 influenza A virus, and an influenza B virus. This preparation and other influenza antigen preparations are described in Palese (2006)[33]. This article and all of its teachings are incorporated herein by reference.

2. Rabies—Rabies is a devastating neurological disease that is caused by infection with the rabies virus. Vaccination against rabies typically utilizes inactivated virus and an aluminum adjuvant. A lipid adjuvant of the oil-in-water type, based on squalene, significantly increased the immunologic response of mice to vaccination with an inactivated virus vaccine when compared to vaccination using an aluminum salt adjuvant (Suli, 2004). An adjuvant based on glycopeptidolipids extracted from *Mycobacterium cheloniae* enhanced the immune response of mice to vaccination with an inactivated rabies virus vaccine (de Souza Matos (2000)[6]).

As part of the present invention, a rabies vaccine may be provided that comprises the extracellular matrix material as the vaccine adjuvant combined with an immunologically effective amount of a rabies antigen. By way of example, a rabies antigen may comprise an inactivated rabies virus. One example of an inactivated rabies virus vaccine antigen that may be used in the present formulations is described in de Souza Matos (2000)[6].

3. Viral Hepatitis—Viral hepatitis, particularly that caused by Hepatitis B virus, is a serious health problem with over 300 million people affected worldwide. Vaccination offers hope for effective prophylaxis. Peptide epitopes of the virus stimulated a significant immune response when fused with heat shock protein 70 from *Mycobacterium* tuberculosis as an adjuvant (Peng (2006)[7]). Unmethylated CpG dinucleotides were effective as an adjuvant with hepatitis B antigen in aged mice (Qin (2004)[8]); and a vaccine consisting of hepatitis B virus antigens and an immunostimulatory DNA sequence is in human clinical trials (Sung (2006)[9]). In development of an intranasal vaccine, it was shown that DL-lactide/glycolide copolymer microspheres with chitosan were an effective adjuvant for a vaccine based on recombinant Hepatitis B surface protein (Jaganathan (2006)[10]).

As part of the present invention, a viral hepatitis vaccine may be provided that comprises the extracellular matrix material as the vaccine adjuvant combined with an immunologically effective amount of a viral hepatitis antigen. By way of example, such a hepatitis antigen may comprise recombinant hepatitis B surface protein. By way of example, such a hepatitis B surface protein antigen is described in Jaganathan, (2006)[10], which reference is specifically incorporated herein by reference.

Vaccines for Disease Associated with Bacterial Infections:

1. Diphtheria—A respiratory disease characterized by dysnepea, weakness, and pyrexia, diphtheria is the result of infection with *Corynebacterium diphtheriae*, bacteria which produces a toxin that is carried hematogenously through the body. Immunization against diphtheria is frequently combined with immunization against tetanus and pertussis; these vaccines typically contain aluminum salt adjuvants (Sugai (2005)[11]). Unmethylated CpG dinucleotides were effective as an adjuvant in a diphtheria-tetanus-pertussis vaccine and shifted the immune response toward cell-mediated immunity in mice immunized intraperitoneally (Sugai (2005)[11]). Trials to reduce adverse side-effects related to the aluminum salt adjuvant of a vaccine consisting of diphtheria toxoid, tetanus toxoid, and purified *Bordetella* pertussis antigens including pertussis toxoid showed that reduction of the aluminum salt content of the vaccine resulted in reduced geometric mean antibody concentrations to the relevant antigens, but did not result in reduction of local or general side effects (Theeten (2005)[12]). Monophosphoryl lipid A was shown in mice to effectively serve as an adjuvant for diphtheria toxin in mice (Caglar (2005)[13]).

As part of the present invention, a diphtheria vaccine may be provided that comprises the extracellular matrix material as the vaccine adjuvant combined with an immunologically effective amount of a diphtheria antigen. By way of example, a diphtheria antigen may comprise a diphtheria toxoid. One example of a diphtheria toxoid that may be used in the practice of the present invention is described in Theeten (2005)[12].

2. Anthrax—Anthrax is a disease caused by the bacterium, *Bacillus anthracis*. Specifically, the bacterium produces a toxin which results in hemorrhagic necrosis of lymph nodes, hematogenous spread, shock, and death. A vaccine consisting of one subunit (protective antigen) of this toxin was shown to protect mice when combined with a microparticle adjuvant administered by either the intramuscular or intranasal routes (Flick-Smith (2002)[14]. Further, vaccination protected mice against infection with *B. anthracis* spores. While the aluminum salt-adjuvanted anthrax-vaccine-adsorbed is the only anthrax vaccine licensed in the United States, major drawbacks exist, including a very lengthy and complicated dosing schedule, followed by annual booster injections. Further, the aluminum adjuvant of anthrax vaccine has been linked to Gulf War Illness among veterans of the 1991 conflict (Petrik (2007))[15].

As part of the present invention, an anthrax vaccine may be provided that comprises the extracellular matrix material as the vaccine adjuvant combined with an immunologically effective amount of an anthrax antigen. By way of example, such an anthrax antigen may comprise the one subunit (protective antigen) of the *Bacillus anthracis* bacterium. One such particular antigenic subunit is described in Flick-Smith (2002)[14].

3. *Streptococcus pneumoniae*—A bacterial pathogen of particular importance to the elderly and young adults, *Streptococcus pneumoniae* causes disease including sepsis and pneumonia, otitis media and meningitis. Vaccines typically involve adsorption of *S. pneumoniae* antigens to aluminum salt adjuvants, and reduced aluminum salt content led to reduced immunogenicity of *S. pneumoniae* vaccines (Levesque (2006)[16]. In human trials, IL-12 failed to improve the immune response to a pneumococcal polysaccharide vaccine; and IL-12 was associated with a high incidence of local and systemic side effects in humans (Hedlund (2002)[17]. Intranasal immunization against *S. pneumoniae* has been shown to be an effective method for preventing infection and disease, with unmethylated CpG dinucleotides serving as an effective adjuvant for an intranasal polysaccharide-protein conjugate vaccine (Sen (2006)[18]). Likewise, IL-12 and the B-subunit of cholera toxin were both shown to enhance efficacy of intranasally-administered preparations of *S. pneumoniae* antigens (Sabirov (2006)19; Pimenta (2006)[20]).

As part of the present invention, a pneumonia vaccine may be provided that comprises the extracellular matrix material described herein as the vaccine adjuvant combined with an immunologically effective amount of a pneumococcal antigen. By way of example, such a pneumococcal antigen may comprise a pneumococcal polysaccharide antigen. One form of a pneumococcal polysaccharide antigen is described in Hedlund (2002)[17]. This pneumococcal antigen may used as part in combination with the herein described adjuvants in a vaccine preparation.

Vaccines for Diseases Associated with Parasitic Infections

1. Malaria—Malaria affects millions of people worldwide and each year, 1-2 million people die from the disease caused by *Plasmodium falciparum*. Thus, the need for prophylactic measures has led to great interest in anti-malaria vaccines. The apical membrane antigen, a malaria vaccine candidate, was reported to have an enhanced immunogenicity by the aluminum salt adjuvant Alhydrogel (HCl Biosector, Denmark); and this adjuvant effect was further enhanced, and shifted from a Th1 response to a mixed Th1/Th2 response, by inclusion of the adjuvant CpG oligodeoxynucleotide (Mullen (2006)[21]). Alhydrogel and Montanide ISA 720 (Seppic, France) were compared in rhesus monkeys as adjuvants for a vaccine based on protective epitopes from the circumsporozoite protein of *P. falciparum*. Though Montanide ISA 720 induced superior immune responses, the formation of sterile abscesses at injection sites were noted as a significant disadvantage (Langermans (2005)[22]). Other studies with a circumsporozoite protein vaccine conducted in rhesus monkeys showed that some novel oil-in-water adjuvants with components of immunostimulants 3-deacetylated monophosphoryl lipid A (3D-MPL) and the saponin *Quillaja saponaria* 21 (QS21) were safe and stimulated improved antibody responses (Stewart (2006)[23]). Some of these same oil-in-water adjuvants improved the immune response to a vaccine constructed of the *P. falciparum* antigen, Liver Stage Antigen-1 (Brando (2006)[24]).

As part of the present invention, a malarial vaccine may be provided that comprises the extracellular matrix material as the vaccine adjuvant combined with an immunologically effective amount of a malarial antigen. By way of example, such a malarial antigen may comprise a *P. falciparum* antigen Liver Stage Antigen-1. This antigen is described in detail in Brando (2006)[24], this article being specifically incorporated herein by reference. This antigen may be combined with the extracellular matrix material described herein as an adjuvant to provide an anti-malarial vaccine as described herein.

2. Leishmaniasis—Leishmaniasis is a parasitic disease associated with infection by a species of parasites from the *Leishmania* genus. A large spectrum of clinical disease forms can result from infection, ranging from cutaneous lesions to fatal visceral forms. In the absence of effective, non-toxic treatments, great effort has been given to vaccine development. Vaccines based on DNA of the parasite have been shown to induce partial protection; aluminum phosphate adjuvant has no effect on the humoral response to this vaccine, but has been reported to slightly increase the cellular immune response and protection against infection in a mouse model (Rosado-Vallado (2005)[25]). In evaluations in rhesus monkeys using a soluble *Leishmania* antigen and alum with IL-12 as adjuvants, it was shown that the adjuvants improved protective immunity, though transient nodules developed at the site of subcutaneous injection (Kenney (1999)[26]). CpG oligodeoxynucleotides served as an effective adjuvant for a vaccine consisting of live, nonattenuated *L. major* organisms alone or in combination with lysates of heat-killed *L. major* promastigotes, either without or bound to alum (Mendez (2003)[27]). Partial protective immunity was stimulated, but mice receiving alum-containing vaccines developed large dermal lesions that required up to 10 weeks to heal.

As part of the present invention, an anti-parasitic infection associated disease vaccine may be provided that comprises the extracellular matrix material as the vaccine adjuvant combined with an immunologically effective amount of a Leishmaniasis antigen, or any of the other antigenic species described above. By way of example, a Leishmaniasis antigen may comprise the Leishmaniasis antigen described in detail in Kenny (1999)[26], which article is specifically incorporated herein by reference.

Vaccines for Disease Associated with Biological Toxins

1. Ricin—Ricin is a toxin produced naturally by the seeds of the castor bean plant, *Ricinus communis*. When humans or animals are exposed to the toxin, severe respiratory distress and death may result. Because of its potency and ability to be administered via aerosol, ingestion, or injection, ricin is considered a powerful bioweapon. Though there is presently no approved commercial vaccine for ricin, pilot trials in humans have examined the use of recombinant, non-toxic forms of one of the subunits of ricin (Vitetta (2006)[28]). This preparation was administered without an adjuvant and elicited ricin-neutralizing antibodies in some of those tested, particularly at higher doses. However, all dose groups were found to result in significant side-effects, including myalgia and headache. Ricin toxoid adjuvantized by liposomal encapsulation was found to induce a stronger immune response when administered intra-tracheally than the vaccine adjuvantized with an aluminum salt adjuvant (Griffiths (1997)[29]). A vaccine consisting of a deglycosylated chain A ricin (DCAR) and the adjuvant LTR72, a mutant of the heat-labile enterotoxin of *Escherichia coli,* resulted in a stronger antibody response of vaccinated mice to ricin, but did not result in improved protection against lung injury when challenged with ricin (Kende (2006)[30]).

As part of the present invention, an anti-ricin vaccine may be provided that comprises the extracellular matrix material as the vaccine adjuvant as described herein combined with an immunologically effective amount of a ricin toxoid antigen. By way of example, such a ricin toxoid antigen is described in detail in Griffiths (1997)[29], which article is specifically incorporated herein by reference.

2. Staphylococcal enterotoxin B (SEB)—SEB is produced by the bacteria, *Staphylococcus aureus* and is associated with food poisoning. Incorporation of SEB toxoid into biodegradable poly(DL-lactide-co-glycolide) microspheres enhanced the immune response of mice to a degree similar to SEB toxoid adsorbed to alum and combined with complete Freund adjuvant (Eldridge, 1991)[31]). Similarly, SEB toxoid was effectively adjuvantized by incorporation into polylactic polyglycolic acid copolymer nanospheres; the resulting immune response was comparable to that achieved by using alum as an adjuvant (Desai (2000)[32]).

As part of the present invention, an anti-toxin-associated disease vaccine may be provided that comprises the extracellular matrix material as the vaccine adjuvant combined with an immunologically effective amount of an antigen such as ricin toxoid or SEB toxoid as antigen. By way of example, such antigens are described in detail in Vitetta (2006)[28] and Eldridge (1991)[31], the teachings of which are specifically incorporated herein by reference.

Vaccines for Diseases Associated with Prions:

In some embodiments, the invention provides an adjuvant preparation that is suitable for use in combination with a prion-associated disease. By way of example, such prion associated diseases include, all of which are classified as transmissible spongiform encephalopathies, bovine spongiform encephalopathy, scrapie, cervid chronic wasting disease and Creutzfeld-Jakob disease.

Although prions use immune and lymphoreticular cells to gain access to the brain (Aguzzi, 2003)[36], existing evidence suggests that humoral immune responses can suppress infection. In particular, antibodies to the cellular prion protein (PrPc) are known to inhibit prion propagation (Petetz, 2001[37]; Enari, 2001[38]). Still, host tolerance to endogenous PrPc remains a major obstacle to active vaccination. In mice, vaccination with recombinant PrPc antigens such as peptides and polypeptides stimulated only weak immune responses. Co-administration of prion antigens with adjuvants such as Freund's (Polymenidou, 2004[39]; Koller, 2002 [40]; Sigurddson, 2002[41]; Gilch, 2003[42]; Hanan, 2001[43]; Hanan, 2001[44]; Souan, 2001[45]; Arbel, 2003[46]); Montanide IMS-1313 (Schwartz, 2003[47]); TiterMax®, a combination of a proprietary block copolymer CRL-8941, squalene, a metabolizable oil, and a unique microparticulate stabilizer (Gilch, 2003[42]); and CpG oligonucleotides (Rosset, 2004[48]) all failed to induce strong immune responses.

It is anticipated that the presently described adjuvant preparations of an extracellular matrix material may be used with the prion protein (PrPc) to provide an improved vaccine against prion-associated infections.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

BIBLIOGRAPHY

The references listed below as well as all references cited in the specification are incorporated herein by reference to the extent that they supplement, explain, provide a background for or teach methodology, techniques and/or compositions employed herein.

1. Higgins D A, et al. (1996), *Vaccine*, 14:478-484.
2. Martin J T. (1997), *Biologicals*, 25:209-213.
3. Banzhoff A, Nacci P, Podda A. (2003), *Gerontology*, 49:177-184.
4. Segura-Velásquez R, et al. (2006), *Vaccine*, 24:1073-1080.
5. Suli J, et al. (2004), *Vaccine* 22:3464-3469.
6. de Souza Matos D C, et al. (2000), *Vaccine*, 18:2125-2131.
7. Peng M, et al. (2006), *Vaccine*, 24:887-896.
8. Qin W, et al. (2004), *Cell Mol Immunol*, 1:148-152.
9. Sung J J, et al. (2006), *Curr Opin Mol Ther* 8:150-155.
10. Jaganathan K S, et al. (2006), *Vaccine*, 24:4201-4211.
11. Sugai T, et al. (2005), *Vaccine*, 23:5450-5456.
12. Theeten H, et al. (2005), *Vaccine*, 23:1515-1521.
13. Caglar K, et al. (2005), *APMIS*, 113:256-263.
14. Flick-Smith H C, et al.(2002), *Infect. Immun.* 70:2022-2028.
15. Petrik M S, et al. (2007), *Neuromolecular Med.* 9:83-100.
16. Levesque P M, et al. (2006), *Hum. Vaccin.* 2:74-77.
17. Hedlund J, et al. (2002), *Vaccine* 20:164-169.
18. Sen G, et al. (2006), *Infect. Immun.* 74:2177-2186.
19. Sabirov A, Metzger D W. (2006), *Vaccine*, 24:5584-5592.
20. Pimenta F C, et al. (2006), *Infect. Immun.*, 74:4939-4944.
21. Mullen G E D, et al. (2006), *Vaccine*, 24:2497-2505.
22. Langermans J A M, et al. (2005), *Vaccine*, 23:4935-4943.
23. Stewart V A, et al. (2006), *Vaccine*, 24:6483-6492.
24. Brando C, et al. (2006), *Infect. Immun. Epub*.
25. Rosado-Vallado M, et al. (2005), *Vaccine*, 23:5372-5379.
26. Kenney R T, et al. (1999), *J. Immunol.*, 163:4481-4488.
27. Mendez S, et al. (2003), *Infect. Immun.*, 71:5121-5129.
28. Vitetta E S, et al. (2006), *Proc. Nat. Acad. Sci.* (USA), 103:2268-2273.
29. Griffiths G D, et al. (1997), *Vaccine*, 15:1933-1939.
30. Kende M, et al. (2006), *Vaccine*, 24:2213-2221.
31. Eldridge J H, et al. (1991), *Infect. Immun.*, 59:2978-2986.
32. Desai M P, et al. (2000), *J. Microencapsul.*, 17:215-225.
33. Palese (2006), *Emerg. Inf. Dis.*, 12 (1): 61-65.
34. Caughey, B. and Baron, G. S. (2006), *Nature* (443(19): 803-810
35. Aguzzi, A. and Heikenwalder, M. (2006), *Nature Reviews/Microbiology*, 4:765-775.
36. A. Aguzzi, F. L. et al. (2003), *Br Med Bull* 66: 141-159.
37. D. Peretz, et al (2001), *Nature* 412: 739-743.
38. M. Enari, et al. (2001), *Proc Natl Acad Sci* USA 98: 9295-9299.
39. Polymenidou M, et al. (2004), *Proc Natl Acad Sci* USA, 101(Suppl. 2): 14670-14676.
40. M. F. Koller, T. et al. (2002), *J Neuroimmunol* 132: 113-116.
41. E. M. Sigurdsson, et al. (2002), *Am J Pathol* 161: 13-17.
42. S. Gilch, F. et al. (2003), *J Biol Chem* 278: 18524-18531.
43. E. Hanan, O. et al. (2001), *Biochem Biophys Res Commun* 280: 115-120.
44. E. Hanan, et al. (2001), *Cell Mol Neurobiol* 21: 693-703.
45. L. Souan, et al. (2001), *Eur J Immunol* 31: 2338-2346.
46. M. Arbel, et al. (2003), *J Neuroimmunol* 144: 38-45.
47. A. Schwarz, et al. (2003), *Neurosci Lett* 350: 187-189.
48. M. B. Rosset, et al. (2004), *J Immunol* 172: 5168-5174.

What is claimed:

1. A composition suitable for use against an infectious pathogen comprising:
    an immunogenic amount of an infectious pathogen or biological toxin antigen preparation of interest; and
    an adjuvant of heterologous extracellular matrix, wherein the immunogenic amount of the infectious pathogen or biological toxin antigen preparation of interest in the presence of the adjuvant is less than the immunogenic amount of the infectious pathogen or biological toxin antigen preparation of interest that elicits a detectable protective response in the absence of the adjuvant, wherein the infectious pathogen antigen preparation of interest comprises an inactivated preparation of the infectious pathogen antigen of interest or toxic products thereof.

2. The adjuvant of claim 1, wherein said infectious pathogen or biological toxin is tetanus, influenza, rabies, viral hepatitis, diphtheria, anthrax, *Streptococcus pneumoniae* infection, malaria, leishmaniasis, ricin toxicosis, prions, or Staphylococcal enterotoxin B toxicois.

3. The composition of claim 1, wherein the infectious pathogen or-biological toxin antigen preparation of interest is tetanus toxoid.

4. The composition of claim 1, wherein the extracellular matrix is a heterologous acellular collagenous tissue preparation.

5. The composition of claim 1, prepared by a method comprising:
    obtaining an adjuvant of an extracellular matrix capable of enhancing the immunogenicity of an infectious pathogen or biological toxin antigen of interest; and
    combining said adjuvant with an immunogenic amount of an infectious pathogen or biological toxin antigen of interest.

6. The composition of claim 1, wherein the infectious pathogen is tetanus.

7. The composition of claim 1, wherein the extracellular matrix comprises a heterologous acellular collagenous tissue preparation.

8. The composition of claim 1, wherein the biological toxin antigen preparation of interest comprises an inactivated preparation of the biological toxin antigen of interest.

9. The composition of claim 1, wherein the extracellular matrix consists essentially of a heterologous acellular collagenous tissue preparation.

10. The composition of claim 9, wherein the adjuvant comprises a 1:10 ratio of the extracellular matrix and a pharmaceutically acceptable carrier solution.

11. The composition of claim 1, wherein the immunogenic amount of the biological toxin antigen preparation of interest is 0.03 μg to 0.05 μg of a tetanus toxoid.

12. The composition of claim 1 comprising a vaccine.

13. A method for immunizing an animal against an infectious pathogen of interest comprising:
    administering an immunogenic amount of the composition of claim 1 composition comprising an infectious pathogen antigen of interest and an infectious pathogen vaccine adjuvant sufficient to stimulate an immune response in said animal for said infectious pathogen of interest or a toxic product produced by said infectious pathogen of interest, wherein the immunogenic amount of the composition sufficient to stimulate an immune response in the animal is less than the immunogenic amount of the infectious pathogen antigen of interest in the absence of the infectious pathogen vaccine adjuvant sufficient to stimulate an immune response.

14. The method of claim 13 wherein the infectious pathogen antigen of interest comprises a tetanus toxoid preparation.

15. The method of claim 13 wherein the immunogenic amount of the composition comprises 0.03 μg to 0.05 μg of the tetanus toxoid.

16. The method of claim 13 wherein an immunized animal has an enhanced survival rate compared to a non-immunized animal.

\* \* \* \* \*